US006902296B2

United States Patent
Searfoss, III

(10) Patent No.: US 6,902,296 B2
(45) Date of Patent: Jun. 7, 2005

(54) NIGHTLIGHT FOR PHOTOTHERAPY

(76) Inventor: Robert Lee Searfoss, III, 1370-3 Chalmette Dr. NE., Atlanta, GA (US) 30306

(*) Notice: Subject to any disclaimer, the term of this patent is extended or adjusted under 35 U.S.C. 154(b) by 193 days.

(21) Appl. No.: 10/461,936

(22) Filed: Jun. 13, 2003

(65) Prior Publication Data

US 2003/0231495 A1 Dec. 18, 2003

Related U.S. Application Data

(60) Provisional application No. 60/389,256, filed on Jun. 15, 2002.

(51) Int. Cl.$^7$ .................................................. F21V 9/00
(52) U.S. Cl. ............................ 362/231; 362/1; 362/2; 362/234; 368/10; 600/27
(58) Field of Search ............................. 362/1, 2, 231, 362/234, 251, 276, 253, 800; 368/10, 72, 83; 600/26, 27

(56) References Cited

U.S. PATENT DOCUMENTS

| | | | |
|---|---|---|---|
| 3,576,185 A | 4/1971 | Schulz et al. .................. 128/1 |
| 3,898,383 A | 8/1975 | Herbits ..................... 179/1 VC |
| 5,008,865 A * | 4/1991 | Shaffer et al. ................. 368/10 |
| 5,046,494 A | 9/1991 | Searfoss et al. ............. 128/395 |
| 5,167,610 A | 12/1992 | Kitado et al. ................. 600/26 |
| 5,197,941 A | 3/1993 | Whitaker ..................... 600/27 |
| 5,242,376 A | 9/1993 | Shealy et al. ................. 600/27 |
| 5,259,830 A | 11/1993 | Masuda ........................ 600/27 |
| 5,265,598 A | 11/1993 | Searfoss et al. ............... 607/88 |
| 5,403,261 A | 4/1995 | Shimizu et al. ............... 600/27 |
| 5,928,133 A | 7/1999 | Halyak ........................ 600/26 |
| 5,954,629 A | 9/1999 | Yanagidaira et al. ......... 600/27 |
| 6,236,622 B1 * | 5/2001 | Blackman .................... 368/72 |
| 6,280,053 B1 | 8/2001 | Chien ......................... 362/228 |
| 6,289,238 B1 | 9/2001 | Besson et al. .............. 600/509 |
| 6,305,821 B1 | 10/2001 | Hsieh et al. ................. 362/246 |
| 6,431,719 B1 * | 8/2002 | Lau et al. .................... 362/800 |
| 2002/0159258 A1 * | 10/2002 | Beeman ....................... 362/231 |

* cited by examiner

Primary Examiner—Stephen F Husar
(74) Attorney, Agent, or Firm—Drummond & Duckworth

(57) ABSTRACT

A nightlight is provided for providing therapeutic effects on the human body and mind including promoting relaxation, sleep and wakefulness. The nightlight includes a housing, a light source, a central processor, one or more controls, and a power supply. The light source produces at least three modes having various light properties. The light modes include a sleep readiness mode, a sleep help mode and a wake-up mode. The sleep readiness mode produces light at about 40 lumens and preferably includes only light from the blue and yellow portions of the visible light spectrum. The sleep help mode produces monochromatic light in the blue or green spectrum. Preferably, the light undulates at a frequency of one cycle per second to one cycle per minute at a luminosity of between 5 lumens and 25 lumens. Meanwhile, the wake-up mode produces substantially full spectrum light at approximately 1,600 lumens. The processor and controls allow a person to select and control the various light modes. Moreover, the nightlight may include biological sensors for measuring physiological activity of the body.

20 Claims, 5 Drawing Sheets

NIGHTLIGHT FOR PHOTOTHERAPY

RELATED APPLICATIONS

This application is a continuation-in-part of my co-pending U.S. Provisional Application Ser. No. 60/389,256, filed Jun. 15, 2002.

BACKGROUND OF THE INVENTION

The present invention relates to "nightlight" type lighting fixtures. Moreover, the present invention relates to lighting apparatus for providing therapeutic effects on the human body and mind.

Human eyes are sensitive to light in a very small region of the electromagnetic spectrum labeled "visible light". This visible light range corresponds to a wavelength of approximately 400–700 nanometers (nm) and a color spectrum of violet through red. As reflected in FIG. 4, the visible colors from shortest to longest wavelength are violet, blue, green, yellow, orange and red.

It has long been recognized that light can have profound psychological as well as physiological effects on the human body. An example of a human organ whose regulatory function is responsive to light is the pineal gland which secretes the hormone melatonin. The hormone is released during periods of darkness, while production is abruptly halted when the eyes perceive bright light. Melatonin is distributed throughout the body via the blood and cerebrospinal fluid and can affect the function of organs by which it is metabolized to influence sleep cycles, feeding cycles, reproduction cycles and other biological rhythms. It has therefore been suggested that phototherapy may effectively be employed to correct melatonin imbalances and correct sleep cycles which may have been altered from stress, jet lag, life in the polar regions, or changes in the sleep pattern.

Additionally, it has been found that some of the body's responses to light are acutely dependant on specific characteristics of the light such as the light's wavelength and intensity. Further, it has been determined that particular bodily responses can be produced or enhanced by varying the light's characteristics according to certain sequences or patterns. For example, U.S. Pat. No. 5,265,598 describes an apparatus for providing a phototherapy method where various isolated electromagnetic energy patterns are directed to an observer's eyes in an effort to induce a state of homeostasis.

Various attempts have been made to develop lighting apparatus in the home for inducing sleep or wake-up. For example, U.S. Pat. No. 6,236,622 describes a nightlight type lighting fixture which incorporates an alarm clock. Moreover, the lighting fixture provides lamp modes including a wake-up cycle and a sleep cycle which gradually increase and decrease according to the desires of the user. U.S. Pat. No. 5,197,941 discloses a travel alarm clock including a lamp, a speaker and an ion generator for producing ionized air. The device is intended to induce sleep and wake cycles by varying the lamp, sound and ion levels. Numerous references including U.S. Pat. Nos. 5,954,629; 5,259,830 and 5,242,376 describe masks or goggles for producing light in specific frequency ranges for inducing sleep. Still additional references including U.S. Pat. No. 5,167,610 and U.S. Pat. No. 5,928,133 disclose apparatus for inducing sleep which include biological monitors for monitoring brainwaves or respiration.

Unfortunately, prior art devices do not provide a natural environment lamp for use in the bedroom which produces light in specific frequency ranges and modes so as to provide therapeutic effects to enhance sleep readiness, sleep help and wake-up.

SUMMARY OF THE INVENTION

Briefly, in accordance with the invention, I provide a nightlight constructed for bedside placement which produces light at specific light wavelengths and intensity to provided physiological effects on the user.

The nightlight includes a housing, one or more lamps for producing a plurality of light modes, a central processor for controlling the operation of the one or more lamps, one or more controls for allowing a user to select the desired lamp modes, and a power supply. The nightlight's housing may be constructed in various forms as can be determined by one skilled in the art. For example, the nightlight's housing may be constructed to look like a conventional nightlight or lamp. Alternatively, the nightlight may be constructed in various geometric shapes such as a cube, pyramid, or sphere. The housing may include a flat base for resting upon a flat surface, or a clip or other fastener for affixing to bedroom furniture. However, it is preferred that the housing is constructed to provide a substantially uniform light for viewing by the user.

Of importance to the practice of the invention, the one or more lamps produce at least three lamp modes including a sleep readiness mode, a sleep help mode, and a wake-up mode. The light produced during the sleep readiness mode is of a frequency and intensity which is ideally suited for relaxation, but preferably of sufficient brightness to allow a person to perform routine tasks, such as to allow one to change into one's bedtime clothes and perform other tasks associated with preparing for sleep. A light producing between 20 lumens and 200 lumens or greater is acceptable. However, it has been found that a lamp producing about 40 lumens of light is preferable for sleep readiness. Moreover, preferably the light produced during the sleep readiness mode is comprised of substantially only light from the blue and yellow portions of the visible light spectrum. Specifically, blue light, and to a lesser extent green light, have been found to have a physiological effect on the human body, promoting relaxation and restfulness. Meanwhile, the addition of yellow light makes the light appear to be a substantially full-spectrum white. This full spectrum appearing light is advantageous for allowing a user to perform simple tasks, while gaining the benefits produced by the illumination in the blue spectrum.

Meanwhile, the light produced by the nightlight in the sleep help mode is intended to further stimulate stage 1 sleep. Preferably, the light produced during the sleep mode is a substantially monochromatic light in the blue to green light range, and at an intensity below that produced during the sleep readiness mode. Preferably, the light is produced at a luminosity of between 5 lumens and 50 lumens. Furthermore, it is preferable that the light has an intensity which varies in a sine wave like pattern. Preferably, this undulation varies between 5 lumens and 25 lumens at a frequency of one cycle per second to one cycle per minute (1 Hz–0.0167 Hz).

The light produced during the wake-up mode provides for physiological effects on the body for aiding a person to wake-up. The illumination produced during the wake-up mode is preferably of substantially full spectrum white light at an intensity brighter than the light produced during the sleep readiness mode or sleep help mode. For example, a preferred luminosity produced during the wake-up mode is between 1,000 lumens and 1,800 lumens. Even more preferably, the light produces approximately 1,600 lumens. This very bright light has been found to retard the production of melatonin in the body and assist in resetting a person's biological clock.

Illumination produced by the sleep readiness mode, sleep help mode and wake-up mode may be accomplished using one or more lamps. For example, a single lamp in cooperation with a plurality of light filters may be used to create the three light modes of varying light frequency and intensity. Alternatively, separate lamps may be used for each lamp mode. In a preferred embodiment, the nightlight includes a plurality of light emitting diodes (LEDs) which produce light in narrow frequency bands which can be used alone or in conjunction to provide the desired properties of the selected light mode.

The nightlight of the present invention further includes a processor and controller for controlling the operations of the nightlight. Preferably, the processor includes circuitry, software and memory for controlling the operation of the respective illumination modes. For example, preferably the processor includes a timer for automatically extinguishing the sleep help mode after a predetermined time period. Furthermore, the processor is connected to the sleep help lamps for controlling the intensity and frequency of the sine wave undulation of the illumination. For example, in a preferred embodiment, the processor automatically decreases the undulation frequency from a rate initially selected by the user. The undulation frequency decreases, thereby increasing the light's sine wave period until the processor's timer deactivates the sleep help mode entirely. The rate of change in undulation frequency is also preferably controllable by the user using the nightlight's controller.

The nightlight's controller includes one or more manually operated control knobs, switches, buttons or touch panels for allowing a user to select the functions of the respective illumination modes. For example, the controller includes at least one knob, button or touch panel or the like for allowing a person to select between the sleep readiness mode, the sleep help mode and the wake-up mode. The controller also allows a person to adjust the processor's timer to allow a person to control the activation period of the sleep help mode. The controller may also include various knobs and/or buttons for allowing the user to adjust the frequency bands and intensity of the light produced by the respective illumination modes, and for allowing the user to control the undulation frequency produced during the sleep help mode. Preferably, selected operations can be stored in the processor's memory for review or adoption at a later date.

Preferably, the processor and controller also allow the user to select an initial undulation frequency.

In still an additional preferred embodiment of the invention, the nightlight includes biological sensors for sensing the biological or physiological activity of the human body. The biological and neurological sensors are provided to sense and measure the individual's homoeostatic state. Sensors may measure one or more of the body's conditions including the user's body temperature, pulse, systolic and/or diastolic blood pressure, respiration, blood oxygen and brainwave electrical activity. The sensors may be connected to the nightlight using direct wiring or wireless or infrared transmitters. Preferably the biological or physiological activity is also recorded in the processor's memory for further review by the user at a later date.

Accordingly, it is a principal object of the invention to provide an improved nightlight which is constructed to be placed and be aesthetically pleasing within the bedroom environment.

It is still an additional object of the present invention to provide a nightlight which is ideally adapted to produce light for enhancing sleep readiness, sleep help and wakefulness.

It is still an additional object of the present invention to provide a nightlight producing numerous illumination modes which are controllable by a user.

Furthermore, it is an additional object of the present invention to include a nightlight including biological and physiological sensors for sensing bodily activities which can be reviewed at a later time.

These and other further and more specific objects and advantages of the invention will be apparent to those skilled in the art from a review of the following detailed description taken in conjunction with the drawings.

DETAILED DESCRIPTION OF THE INVENTION

Figure 1:
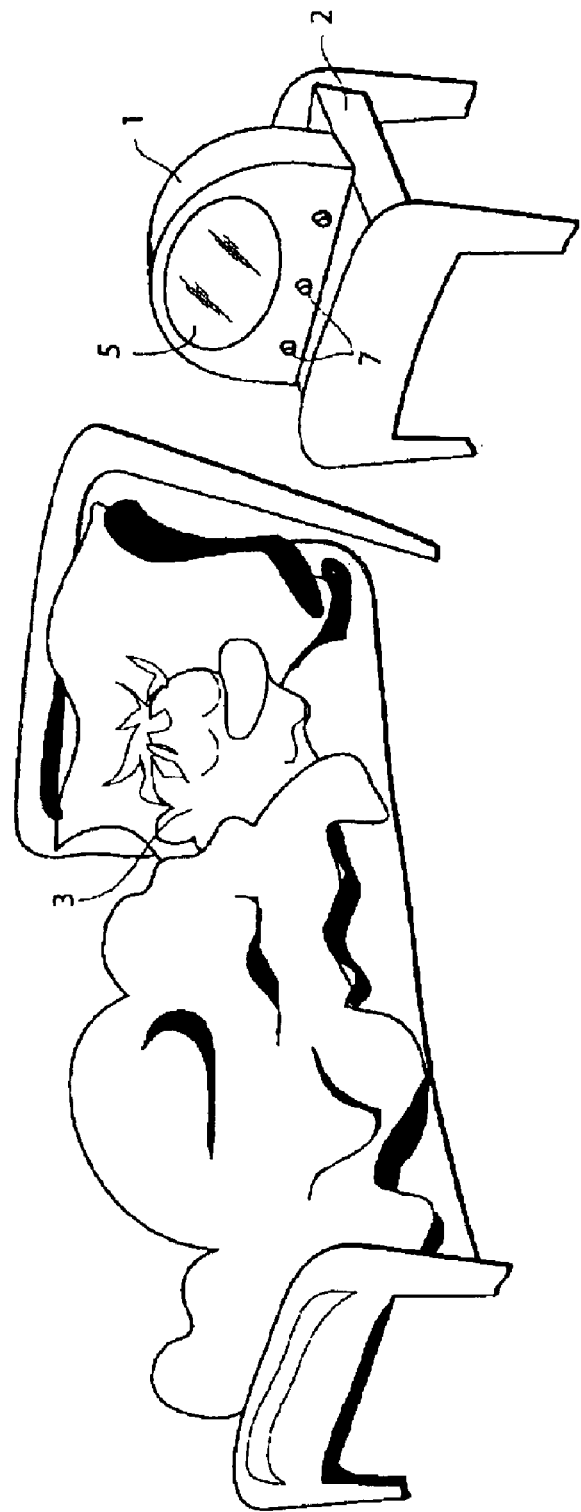
FIG. 1 is a perspective view illustrating a person utilizing the nightlight of the present invention.
Figure 2:
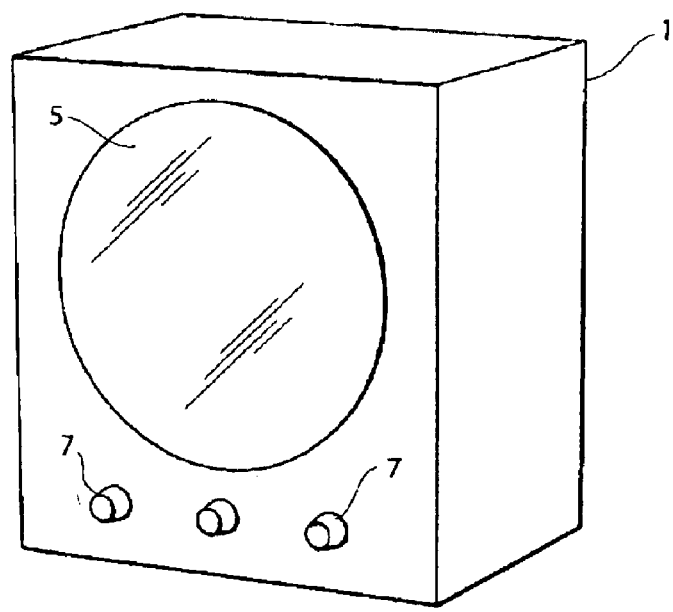
FIG. 2 is a perspective view of an embodiment of a nightlight of the present invention.
Figure 3:
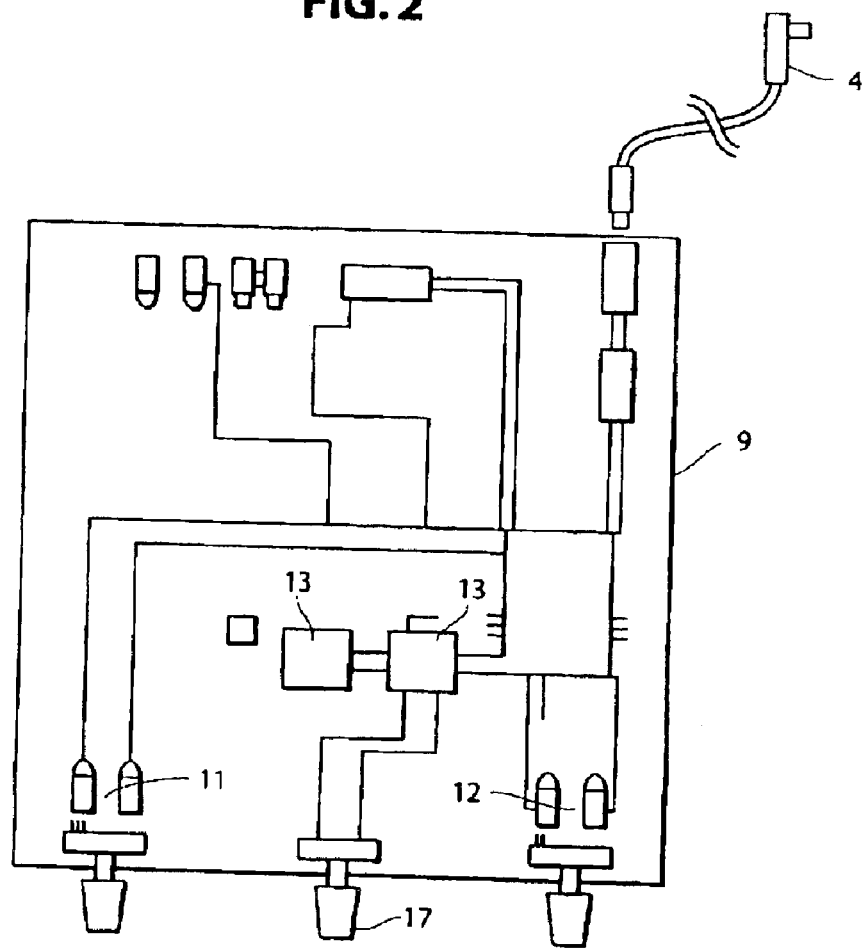
FIG. 3 is a plan view showing a processor for use with the nightlight of the present invention.
Figure 4:
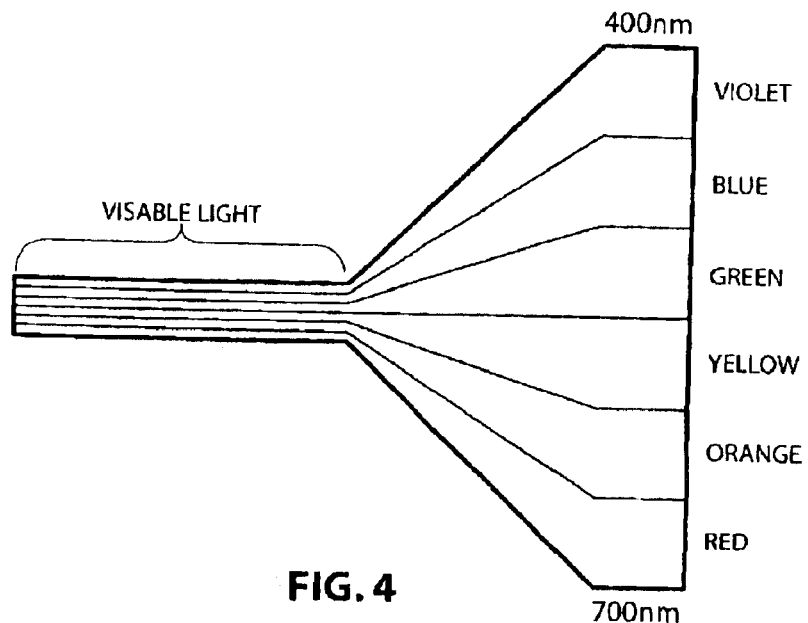
FIG. 4 is a graph illustrating the wavelengths in the visible light spectrum.

While the present invention is susceptible of embodiment in various forms, as shown in the drawings, hereinafter will be described the presently preferred embodiments of the invention with the understanding that the present disclosure is to be considered as an exemplification of the invention and is not intended to limit the invention to the specific embodiments illustrated.

With reference to the figures, the present invention is directed to a nightlight 1 which produces light at various preselected intensities and wavelengths which are ideally suited for promoting physiological and therapeutic effects on the human body. In particular, the nightlight 1 provides light modes which promote relaxation, induce stage 1 sleep, and enhance wakefulness. The nightlight includes a housing, a light source 10–12, a central processor 13, a controller 7 and a power supply 4.

As shown in the figures, the housing may be constructed in any number of shapes which are aesthetically pleasing for placement in a bedroom or upon a bedside table 2. Preferably, the housing includes a screen 5 which diffuses the light over a broad surface area to provide a more pleasing and uniform illumination. The light source may include one or more lamps for producing a plurality of lamp modes, each producing light at different intensity and/or frequency bands. The light source may include one or more incandescent bulbs, flourescent bulbs, or light emitting diodes (LEDs), or the like. Moreover, the light source may utilize filters for filtering the light into a desired intensity or frequency bands. However, it is preferred that the nightlight 1 of the present invention include at least three sets of LED lamps 10–12 for producing the various light modes. Though the lamps may produce any number of light modes producing illumination at various intensities and wavelengths, preferably the light modes include at least three modes including sleep readiness mode, a sleep help mode, and a wake-up mode.

The sleep readiness mode produces a light which is of a frequency and intensity which is ideally suited for relaxation. The light produced is preferably dim so as to promote relaxation, but of a sufficient brightness to allow a person to perform simple tasks such as change one's clothes or brush one's teeth. In a preferred embodiment, the sleep readiness mode produces light at between 20–200 lumens. However, a lamp producing about 40 lumens is even more preferred.

Figure 5:
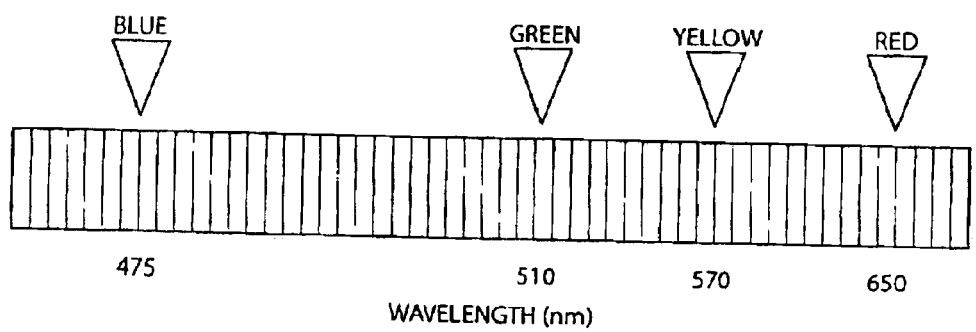
FIG. 5 is a second graph illustrating the wavelengths in the visible light spectrum.
Figure 6:
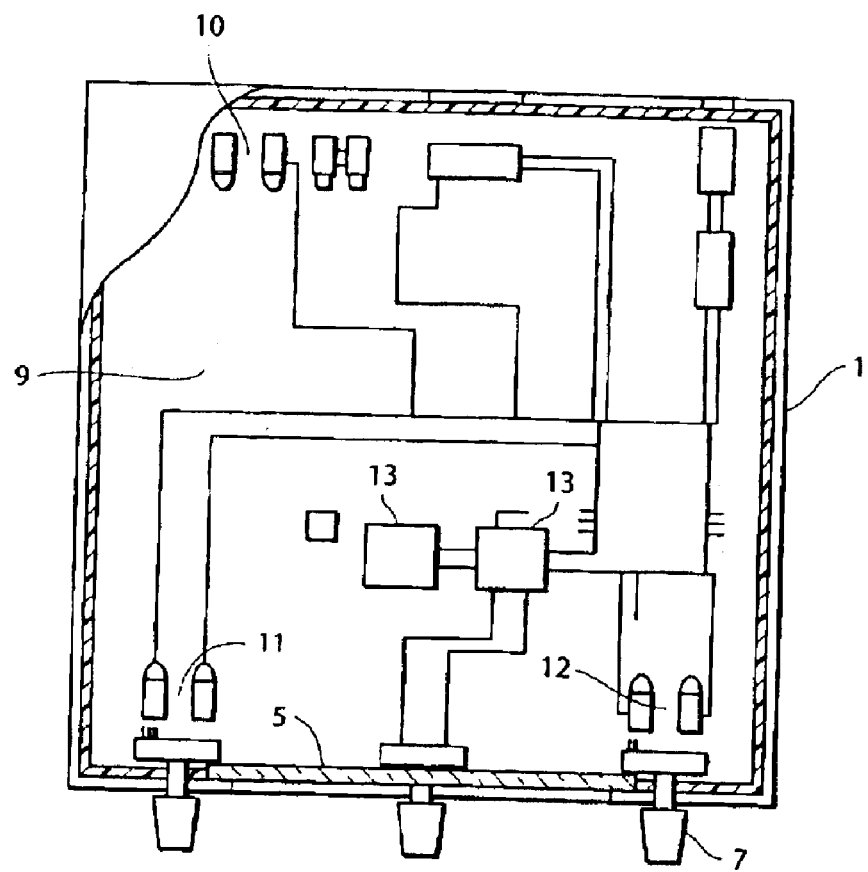
FIG. 6 is a cutaway plan view of the nightlight of the present invention including a plan view of the processor.
Figure 7:
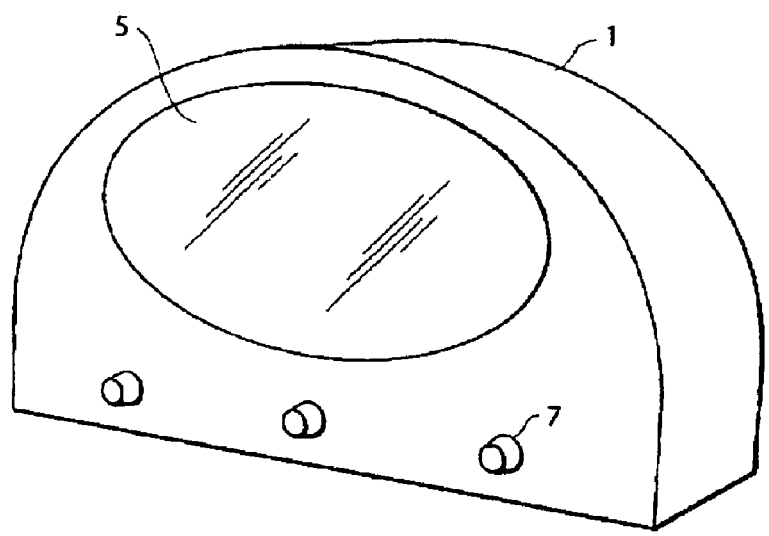
FIG. 7 is a perspective view showing a second embodiment of the nightlight of the present invention.

With reference to FIG. 5, preferably the sleep readiness mode produces light substantially from the blue (approximately 475 nm) and yellow (approximately 570 nm) portions of the light spectrum. The blue light produces a physiological and psychological effect on the human body, particularly restfulness. The green portion of the electromagnetic portion to a lesser extent also promotes restfulness and thus can be produced during the sleep readiness mode. However, blue light is preferred. Meanwhile, the addition of yellow light to the'sleep readiness mode makes the light appear to be substantially full spectrum, or in other words white. This white light appears more traditional to a person 3, and conducive to allowing a person to perform simple tasks while readying one's self for bed.

In addition to a mode for promoting sleep readiness, the nightlight 1 includes a mode for facilitating stage 1 sleep. This sleep help mode utilizes one or more LED lamps 10–12 to produce illumination in a substantially narrow 30 nm frequency band of the visual spectrum. This narrow band of light appears monochromatic in color and is preferably in the blue to green visual light band stretching from approximately 450 nm–540 nm. Preferably, the light produced during the sleep help mode is at a luminosity below that produced during sleep readiness such as between 5 lumens and 50 lumens. Even more preferably, the sleep help mode produces a light of an undulating intensity, increasing and decreasing in a rhythmic pattern. Preferably, the undulation varies the luminosity of the light between 5 lumens and 25 lumens in a sine wave pattern of increasing and decreasing intensity. Moreover, it is preferred that the undulation frequency is controllable from approximately one cycle per second to one cycle per minute (1 Hz–0.0167 Hz).

In still an additional preferred embodiment of the sleep help mode, the nightlight 1 includes a plurality of LED lights, each producing monochromatic light across the visible spectrum. Individual lamps or combinations of lamps may be selected by the user 3 to produce colors that the user finds particularly appealing or soothing. Though the user may select colors stretching across the visible light spectrum, monochromatic blue-green light is preferred.

In addition to inducing sleep, the nightlight 1 of the present invention also includes a light mode for promoting wakefulness. To this end, the nightlight 1 includes one or more lamps that are activated in a wake-up mode. The wake-up mode preferably produces a substantially white light at an intensity brighter than the light produced during the sleep readiness mode or sleep help mode. Preferably, the wake-up mode illumination is a very bright light, such as between 1,000 and 1,800 lumens, so as to retard the production of melatonin in the body, and thereby assist a person in resetting their circadian rhythm. LEDs may be utilized to produce the substantially full spectrum of light of the wake-up mode. However, due to the high luminosity of the wake-up mode, preferably about 1,600 lumens, a more conventional incandescent or flourescent bulb may also be used.

The nightlight 1 of the present invention further includes a processor 9 and controller 7 which cooperatively control and select the various functions of the nightlight. The processor 9 is preferably a printed circuit board (pcb) including one or more microprocessors or memory chips 13 for processing and storing various information. Moreover, the processor includes internal timers and software for controlling the various individual functions of the sleep readiness mode, sleep help mode and wake-up mode. For example, preferably the processor includes a timer for automatically extinguishing the sleep help mode after a predetermined time period. Moreover, the processor preferably controls the voltage and current to the lamps to control the intensity and undulation frequency of the light produced during the sleep help mode. Preferably, the processor also allows the user to automatically decrease the undulation frequency from a rate initially selected. As the undulation frequency decreases, the light's sine wave period correspondingly increases. Preferably, this continues until the processor's timer deactivates the sleep help mode entirely.

The nightlight's controller includes one or more knobs, buttons, switches or the like for controlling the functions of the nightlight. These controls allow a person 3 to select between respective light modes. Preferably, the control panel also allows a person to adjust the sleep help mode's activation period to allow the user to vary the period that the sleep help mode lights are activated before automatically extinguished by the timer. The controller 7 may also allow a user to adjust the intensity or frequency bands of the light produced by the respective illumination modes. Moreover, the controller allows a user to select desired undulation frequencies of the sleep help mode and select whether the undulation frequency automatically decreases over time. The rate of change in undulation frequency is also preferably controllable by the user using the nightlight's controller 7.

Figure 8:
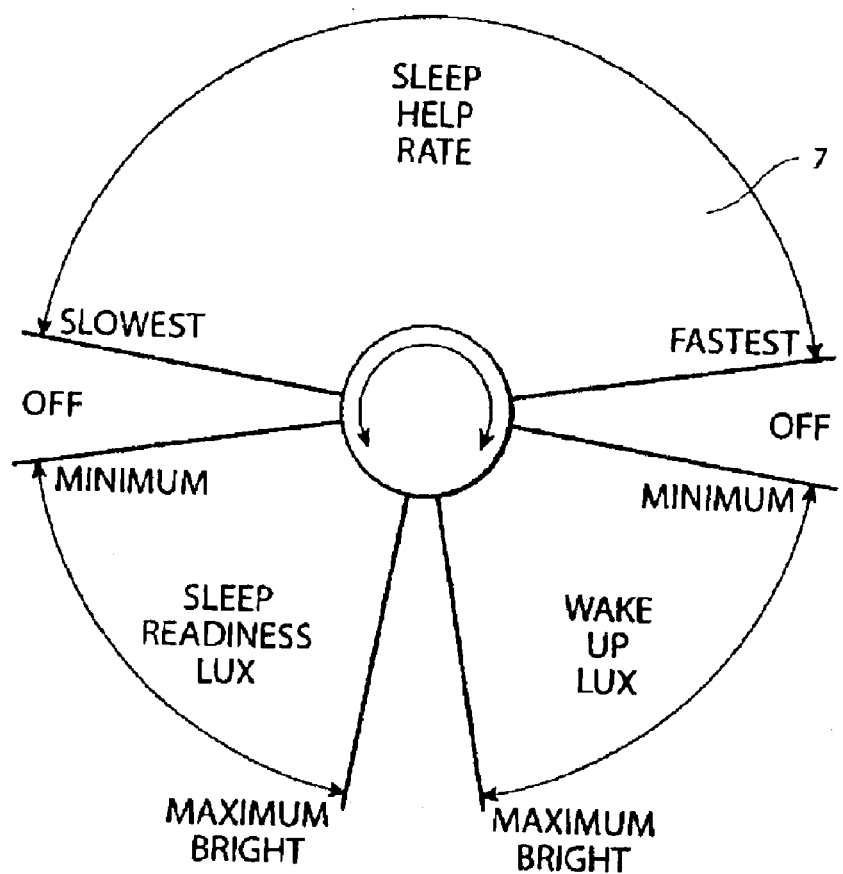
FIG. 8 is a front view illustrating a controller for use with the nightlight of the present invention.

With reference to FIG. 8, a preferred controller for use with the nightlight includes a large dial 7 which can be rotated to control operation of the nightlight. Not only does rotation of the dial allow a person to select a desired sleep mode, but the dial allows a person to adjust the intensity of the light produced during the sleep readiness mode and wake-up mode, and adjust the undulation frequency of the light produced during the sleep help mode.

Though not shown in the figures, the nightlight may include one or more biological sensors. Sensors can be selected by one skilled in the art for measuring a body's temperature, pulse, blood pressure, respiration, blood oxygen content and/or brainwave activity. The sensors may be utilized for automatically selecting a particular light mode. For example, a person may recline in bed and allow the nightlight to automatically transition from sleep readiness mode to sleep help mode based upon physiological indicators such as a reduction of pulse rate or respiration below a threshold level. Moreover, the biological sensors can be used to trigger the wake-up mode, such as a measurement of brainwave activity indicating that the person is waking up. Preferably the biological or physiological activity measured by the sensors is recorded in the processor's memory 13 for later review.

Having described my invention in such terms to enable those skilled in the art to make and use it, and having identified the presently preferred embodiments thereof, I claim:

1. A nightlight comprising:

an illumination means for producing at least three light modes, said light modes including;

a sleep readiness mode producing light appearing as substantially white light;

a sleep help mode producing only substantially blue light or green light;

a wake-up mode producing substantially white light at an intensity brighter than the light produced by said sleep readiness mode or said sleep help mode; and a controller for allowing a person to select said sleep readiness mode, said sleep help mode or said wake-up mode.

2. The nightlight of claim 1 wherein said white light of said sleep readiness mode includes substantially only blue light and yellow light.

3. The nightlight of claim 1 further comprising biological monitors for monitoring the biological functions of a person.

4. The nightlight of claim 1 wherein said sleep help mode produces a light of an undulating intensity.

5. The nightlight of claim 1 wherein said sleep help mode produces a light of an undulating substantially sine wave intensity.

6. The nightlight of claim 1 wherein controller allows a person to select said sleep help mode undulation frequency.

7. The nightlight of claim 5 wherein the undulation frequency automatically decreases over time.

8. The nightlight of claim 1 wherein said sleep help mode produces narrow band light substantially within a 30 nanometer wavelength band.

9. The nightlight of claim 5 wherein said sleep help mode produces narrow band light substantially within a 30 nanometer wavelength band with a luminosity that undulates between about 5 lumens and 25 lumens.

10. The nightlight of claim 1 wherein said sleep help mode will automatically discontinue at predetermined time period after being selected.

11. The nightlight of claim 1 wherein said sleep readiness light includes substantially only blue light and yellow light; said sleep help mode produces a substantially monochromatic light in wavelength band of 30 nanometers which undulates in intensity.

12. A nightlight comprising:

an illumination means for producing at least three light modes, said light modes including;

a sleep readiness mode producing light appearing to be substantially full spectrum light at about 40 lumens;

a sleep help mode producing substantially only blue light or green light, said sleep help mode producing a light of a substantially undulating sine wave intensity between about 5 lumens and 25 lumens with said undulation frequency being controllable;

a wake-up mode producing substantially white light at about 1,000 to 1,800 lumens; and a controller for allowing a person to select said sleep readiness mode, said sleep help mode or said wake-up mode, and for allowing a person to select the undulation frequency of said sleep help mode.

13. The nightlight of claim 12 wherein said white light of said sleep readiness mode includes substantially only blue light and yellow light.

14. The nightlight of claim 12 wherein said sleep help mode will automatically discontinue at predetermined time period after being selected.

15. The nightlight of claim 12 further comprising biological monitors for monitoring the biological functions of a person.

16. The nightlight of claim 12 wherein the undulation frequency automatically decreases over time.

17. A nightlight comprising:

an illumination means for producing at least three light modes, said light modes including;

a sleep readiness mode producing a constant light at between 20 and 200 lumens;

a sleep help mode producing only substantially blue light or green light;

a wake-up mode producing substantially white light at an intensity brighter than the light produced by said sleep readiness mode or said sleep help mode; and a controller for allowing a person to select said sleep readiness mode, said sleep help mode or said wake-up mode.

18. The nightlight of claim 17 wherein said sleep help mode produces a light of an undulating intensity.

19. The nightlight of claim 18 wherein said sleep help mode produces a light of an undulating substantially sine wave intensity varying between about 5 lumens and 25 lumens.

20. The nightlight of claim 18 wherein said wake-up mode produces a light at between about 1,000 lumens and 1,800 lumens.

* * * * *